US009506923B2

(12) United States Patent
Endo et al.

(10) Patent No.: US 9,506,923 B2
(45) Date of Patent: Nov. 29, 2016

(54) METHOD OF DIAGNOSING SURGICAL SITE INFECTIONS

(75) Inventors: Shigeatsu Endo, Iwate (JP); Yasuo Fukui, Kochi (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 0 days.

(21) Appl. No.: 14/238,468

(22) PCT Filed: Aug. 10, 2012

(86) PCT No.: PCT/JP2012/070428
§ 371 (c)(1),
(2), (4) Date: Feb. 11, 2014

(87) PCT Pub. No.: WO2013/024798
PCT Pub. Date: Feb. 21, 2013

(65) Prior Publication Data
US 2014/0212894 A1    Jul. 31, 2014

(30) Foreign Application Priority Data
Aug. 12, 2011 (JP) ................................. 2011-176549

(51) Int. Cl.
G01N 33/00       (2006.01)
G01N 33/569      (2006.01)
G01N 33/68       (2006.01)

(52) U.S. Cl.
CPC .... G01N 33/56966 (2013.01); G01N 33/6893 (2013.01); G01N 2333/70596 (2013.01); G01N 2800/26 (2013.01)

(58) Field of Classification Search
CPC .............. G01N 33/00; G01N 33/56966; G01N 33/6893; G01N 2333/70596; G01N 2800/26
See application file for complete search history.

(56) References Cited

U.S. PATENT DOCUMENTS

| 4,444,879 A * | 4/1984 | Foster ................. G01N 33/545 422/400 |
| 5,420,016 A * | 5/1995 | Boguslaski ............. C12Q 1/04 106/2 |
| 2002/0019018 A1 | 2/2002 | Christopherson et al. |
| 2006/0068445 A1 | 3/2006 | Furusako et al. |
| 2011/0086381 A1 * | 4/2011 | Naito ............................. 435/29 |
| 2012/0309025 A1 | 12/2012 | Okamura et al. |

FOREIGN PATENT DOCUMENTS

| CN | 1334922 A | 2/2002 |
| WO | 96/32418 A1 | 10/1996 |
| WO | 02/47008 A1 | 6/2002 |
| WO | 02/074789 A2 | 9/2002 |
| WO | 2011/093459 A1 | 8/2011 |

OTHER PUBLICATIONS

Yaegashi et al., Evaluation of a newly identified soluble CD14 subtype as a marker for sepsis, J Infect Chemother (2005) 11: pp. 234-238.*
Takahashi et al., Severity assessment of sepsis by determination of the soluble CD14 subtype using the POC test, Medical Postgraduates vol. 48, No. 1, 2010, pp. 25-27.*
Phys Org., Study examines sepsis and septic shock after surgery, Arch Surg. Jul. 19, 2010; 145 (7), pp. 1-2.*
Shindan to Chiryo; JCLS; 2008; 96(1): 61-66, only as described in applicants specification.
M. Sigfrido Rangel-Frausto, et al.; The Natural History of the Systemic Inflammatory Response Syndrome (SIRS); JAMA; Jan. 11, 1995; vol. 273, No. 2; 117-123.
Mirjam Christ-Crain, et al.; Procalcitonin in bacterial infections—hype, hope, more or less?; Swiss Med Wkly; 2005:135: 451-460.
International Search Report of PCT/JP2012/070428 dated Nov. 27, 2012.
Burgmann et al., "Increased Serum Concentration of Soluble CD14 Is a Prognostic Marker in Gram-Positive Sepsis," Clinical Immunology and Immunopathology, 1996, vol. 80(3), Article No. 0128, pp. 307-310.
DuPont et al., "The value of C-reactive protein for postoperative monitoring of lower limb arthroplasty," Annales de Readaptation et de Medecine Physque, 2008, vol. 51, pp. 348-357.
European Search Report, Dec. 15, 2014, European Patent Application No. 12 82 4297, 3 pages.
Shozushima et al., "Usefulness of presepsin (sCD14-ST) measurements as a marker for the diagnosis and severity of sepsis that satisfied diagnostic criteria of systemic inflammatory response syndrome," J. Infect. Chemother., May 2011, DOI 10.1007/s10156-011-0254-x, 6 pages.

* cited by examiner

*Primary Examiner* — Gary W Counts
(74) *Attorney, Agent, or Firm* — Kilpatrick Townsend & Stockton LLP

(57) ABSTRACT

A marker useful in diagnosing surgical site infections is provided. In the method of the present invention for detecting surgical site infections, sCD14-ST in a sample is measured.

9 Claims, 1 Drawing Sheet

```
SEQUENCE LISTING

<160> NUMBER OF SEQ ID NOS: 2

<210> SEQ ID NO 1
<211> LENGTH: 11
<212> TYPE: PRT
<213> ORGANISM: Homo sapiens

<400> SEQUENCE: 1

Thr Thr Pro Glu Pro Cys Glu Leu Asp Asp Glu
1               5                   10

<210> SEQ ID NO 2
<211> LENGTH: 16
<212> TYPE: PRT
<213> ORGANISM: Homo sapiens

<400> SEQUENCE: 2

Arg Val Asp Ala Asp Ala Asp Pro Arg Gln Tyr Ala Asp Thr Val Lys
1               5                   10                  15
```

METHOD OF DIAGNOSING SURGICAL SITE INFECTIONS

CROSS-REFERENCE TO RELATED APPLICATIONS

This application is a national phase application under 35 U.S.C. 371 claiming priority to PCT/JP2012/070428, filed Aug. 10, 2012, which application claims priority to JP 2011-176549, filed Aug. 12, 2011, the teachings of which are hereby incorporated by reference in their entireties for all purposes.

TECHNICAL FIELD

The present invention relates to a method of diagnosing surgical site infections and a kit for carrying out the method.

BACKGROUND ART

Surgical operations are carried out in a variety of fields, including surgery, along with the development of medical technology, and surgical site infections have attracted attention as a risk.

Infections in the surgical field are caused in the perioperative period before or after surgery. More particularly, as infections before surgery, peritonitis (intraperitoneal abscess), severe pancreatitis, and severe intestinal ischemia are known. As for infections after surgery, intraperitoneal abscess, catheter infection, pneumonia, and urinary tract infection are known. Surgical site infections exhibit high severity, and a fast, accurate diagnosis is required for early treatment decisions.

In the current diagnosis of surgical site infections, blood culture, white blood cell count, body temperature, diagnostic imaging, the duration of systemic inflammatory response syndrome (SIRS), blood biochemical findings such as a C-reactive protein (CRP) value, and the like, are used as an index. Of these indices, blood culture shows a low positive rate for infections, and requires 3 to 7 days to obtain the test results, and thus, it is difficult to reflect the treatment at present (Non-patent literature 1). Further, fever and increase in white blood cell count and CRP level immediately after surgery are natural results, and thus, these are not specific indices (Non-patent literature 2). Although it is known that a transition risk to multiple organ failure is increased when the number of SIRS-positive items is increased, the duration varies (about 1 to 3 days) due to surgical stress, and thus, the number of SIRS-positive items is not a specific marker for infection. In addition, procalcitonin (PCT) has recently come to be widely used as a bacterial infection marker, but it is known that its blood level is increased even due to injury, which is not accompanied by infection and is highly invasive, and that the PCT produces a false-positive result in an infection diagnosis (Non-patent literature 3).

As described above, no markers effective in the diagnosis of surgical site infections have been reported yet, and doctors are really struggling against the diagnosis of surgical site infections, and the discovery of such markers is highly desired.

CITATION LIST

Non-Patent Literature

[Non-patent literature 1] JAMA. 1995; 273(2): 117-123
[Non-patent literature 2] Shindan to Chiryo (diagnosis and treatment). 2008; 96(1): 61-66
[Non-patent literature 3] Swiss Med Wkly. 2005; 135 (31-32): 451-460

SUMMARY OF INVENTION

Technical Problem

After surgical site infections are suspected, a quick determination of a proper course of treatment is required. An object of the present invention is to provide a marker effective in the diagnosis of surgical site infections.

Solution to Problem

The present inventors conducted intensive study to solve the object, and found that when surgical site infections are suspected, sCD14-ST, which is a specific marker that reacts with an infection without being affected by surgery (injury), is measured, and surgical site infections could be detected on the basis of its degree or measured value, and the present inventors completed the present invention.

The present invention relates to the following aspects:

Aspect (1) a method of detecting surgical site infections, characterized by measuring sCD14-ST in a sample;

Aspect (2) a method of detecting surgical site infections, comprising the steps of: measuring sCD14-ST in a sample collected from a patient suspected of having a surgical site infection or a patient suffering from a surgical site infection, and
judging that the patient suffers from a surgical site infection when an sCD14-ST value is higher than that of an uninfected person;

Aspect (3) the method according to aspect 2, wherein the sCD14-ST value is compared in the judgment step to a threshold previously determined;

Aspect (4) the method according to any one of the above aspects 1 to 3, wherein sCD14-ST is measured by an immunoassay; and Aspect (5) a kit for detecting surgical site infections, comprising:
(a) an antibody specific to sCD14-ST,
(b) standard data showing a correlation between the amount of sCD14-ST in a sample and surgical site infections, and
(c) an instruction manual.

The term "human sCD14-ST" (also referred to as Presepsin (registered trademark)) as used herein means the "soluble CD14 antigen of the first aspect" disclosed in Japanese Patent No. 4040666 and, more particularly, is a soluble CD14 antigen with the following characteristics 1) to 3):

1) Having a molecular weight of 13±2 kDa as measured by SDS-PAGE under non-reducing conditions;
2) Having the amino acid sequence of SEQ ID NO: 1 at the N-terminal sequence; and
3) Binding specifically to an antibody prepared by using a peptide consisting of 16 amino acid residues of SEQ ID NO: 2 as an antigen.

```
SEQ ID NO: 1:
Thr Thr Pro Glu Pro Cys Glu Leu Asp Asp Glu
1               5                   10

SEQ ID NO: 2:
Arg Val Asp Ala Asp Ala Asp Pro Arg Gln Tyr Ala Asp
1               5                   10

Thr Val Lys
    15
```

The term "infections" as used herein include infections by bacteria, fungi, parasites, or viruses.

The method of confirming the presence of infection is not particularly limited, but examples thereof include, in addition to a commonly-used blood culture, gene identification methods (such as PCR and RP-PCR), diagnostic imaging, ultrasonic diagnosis, endoscopy, and biopsy [Am. J. Infect. Control, 1988; 16: 128-140].

The term "surgical site infections" as used herein means infectious diseases which are caused after surgery, and includes all infections due to surgery and adjunctive therapy needed therefor. Therefore, all infections, such as an infection in which lesions are associated with the surgical operation site, an infection in which lesions are not associated with the surgical operation site, a topical infection, and a systemic infection, are included. Additionally, even if it is an infection which is caused after hospital discharge, or an infection which is caused by surgery conducted in another hospital, these are included, so long as they are caused by treatment or site associated with surgery.

GUIDELINE FOR PREVENTION OF SURGICAL SITE INFECTION, 1999 is published by the Center for Disease Control and Prevention (hereinafter referred to as CDC), and diagnostic criteria, surgery, treatment, prevention, and the like are disclosed [INFECTION CONTROL AND HOSPITAL EPIDEMIOLOGY 1999; 20(4): 247-278]. This document also discloses that currently, surgical procedures per year is 27 million cases, and that CDC's National Nosocomial Infections Surveillance (hereinafter referred to as NNIS) system was established in 1970, and monitors nosocomial infections in acute-care hospitals. Based on NNIS system reports, surgical site infections (hereinafter referred to as SSIs) are the third most frequently reported nosocomial infection, accounting for 14% to 16% of all nosocomial infections among hospitalized patients. During 1986 to 1996, hospitals conducting SSI surveillance in the NNIS system reported 15,523 SSIs following 593,344 operations (CDC, unpublished data). Among surgical patients, SSIs were the most common nosocomial infection, accounting for 38% of all such infections. Of these SSIs, two thirds were confined to the incision, and one third involved organs or spaces accessed during the operation. When surgical patients with nosocomial SSI died, 77% of the deaths were reported to be related to the infection, and the majority (93%) were serious infections involving organs or spaces accessed during the operation. In 1980, Cruse estimated that an SSI increased a patient's hospital stay by approximately 10 days and cost an additional $2,000. A 1992 analysis showed that each SSI resulted in 7.3 additional postoperative hospital days, adding $3,152 in extra charges. As described above, it is corroborated that SSIs increase the hospital days and the cost, and thus, it is desired to diagnose and treat SSIs at an early stage.

The term "sepsis" as used herein means a systemic inflammatory response syndrome (SIRS) which is caused by a bacterial infection. That is to say, sepsis is a very severe state in which a bacterial infection has spread throughout the body, and some of the patients without treatment result in death due to shock, DIC, multiple organ failure, or the like. "Sepsis" means a state where a patient satisfies, in addition to the presence of the above-mentioned infection, for example, two or more criteria out of the following four criteria, which are the criteria for the diagnosis of systemic inflammatory response syndrome (SIRS) [Chest, 1992; 101 (6): 1644-1655]:

1) Body temperature >38° C. or <36° C.;
2) Heart rate >90 per minute;
3) Respiration rate >20 per minute or $PaCO_2$ >32 torr; and
4) White blood cell count >12,000, <4,000/m$^3$ or immature leukocytes >10%;

The term "sepsis" as used herein includes sepsis associated with the final stage of sepsis, and the onset of "severe sepsis", "septic shock", and "complications of sepsis" (for example, multiple organ dysfunction syndrome (MODS), disseminated intravascular coagulation (DIC), acute respiratory distress syndrome (ARDS), and acute renal failure (AKI)), and includes all stages of sepsis, which is not limited.

Although sepsis can be treated by the use of antibiotics or supportive therapy, it remains a serious cause of mortality. According to an estimation in a recent study, 751,000 cases of severe sepsis occur every year in the United States, and the mortality rate thereof is 30 to 50%. The specialists of intensive care or infectious diseases who belong to the Society of Critical Care Medicine (SCCM), the European Society of Intensive Care Medicine (ESICM), and the ISF (International Sepsis Forum) have set up an international program called the "Surviving Sepsis Campaign (SSC)" in 2002 in order to reduce the mortality rate of severe sepsis by 25% during the next 5 years, and the Surviving Sepsis Campaign guidelines (SSCG) have been prepared as part of the approach. This guideline was published in 2004 as a guideline for the diagnosis/treatment of severe sepsis which is first based on evidence, and the revised edition thereof was published in 2008 [Crit. Care. Med., 2008; 36: 296-327]. These guidelines are based on an initial fluid therapy (early-goal directed therapy) or the like for severe sepsis [New Engl. J. Med., 2001; 345: 1368-1377].

Examples of the treatments for sepsis described in the present guidelines include the use of antimicrobial agents, fluid therapy, vasoconstrictors, cardiac drugs, steroid therapy, blood preparations, blood sugar control, blood purification methods [for example, continuous hemofiltration (CHF), continuous hemodiafiltration (CHDF), and hemodialysis (HD)], surgery (for example, abscess drainage and removal of infected necrotic tissues), and the like, as well as an endotoxin adsorption therapy (PMX) and γ-globulin preparations [Crit. Care Med., 2008; 36: 296-327]. The therapeutic agents for sepsis are not limited to the drugs described above, and it is possible to refer to, for example, "Konnichi no Chiryo-yaku—Kaisetsu to Binran 2006 (Therapeutic Drugs of Today—Explanations and Manuals 2006)", edited by Yutaka MIZUSHIMA, Nankodo Co., Ltd., 2006, or the like.

Advantageous Effects of Invention

According to the method of the present invention, the onset of surgical site infections can be detected rapidly and accurately, and thus, an appropriate course of treatment can be determined. For example, a conventional marker (procalcitonin) increases due to the effects of surgery operation, and thus, an infection after surgery cannot be distinguished from the effects of surgery operation. However, the marker (sCD14-ST) used in the present invention is not affected by surgery, and thus, an infection after surgery can be specifically detected.

The kit of the present invention can be used in the method of the present invention.

DESCRIPTION OF EMBODIMENTS

Figure 1:
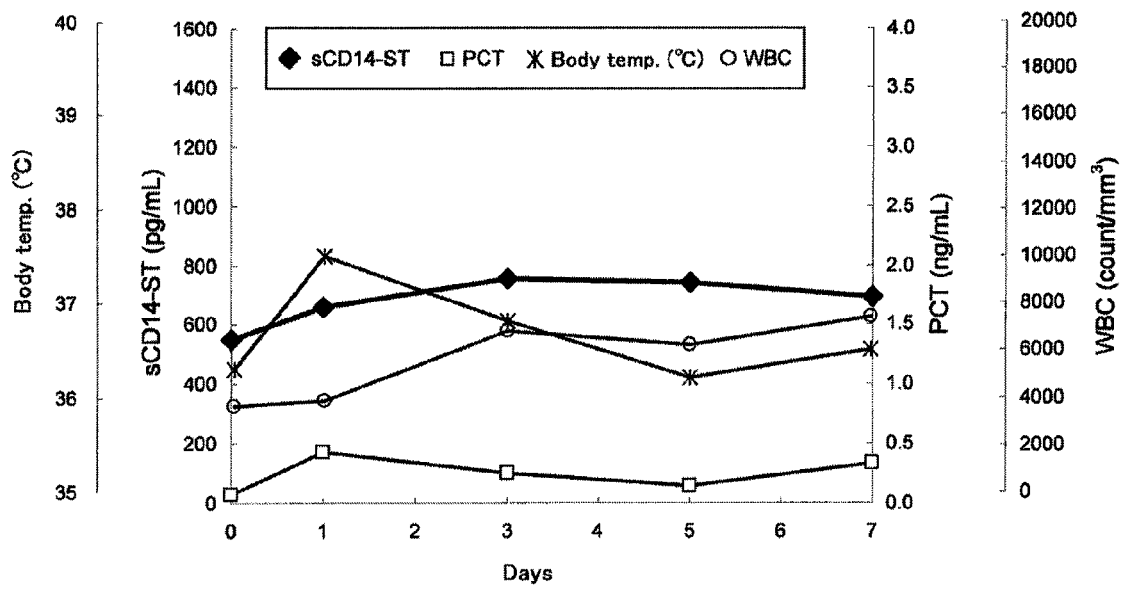
FIG. 1 is a graph showing the changes in each index (sCD14-ST, PCT, body temperature, and WBC) in a case in which no surgical site infections were caused.

In the detection method of the present invention (hereinafter referred to as the method of the present invention), sCD14-ST in a sample collected from a subject, in particular, a patient suspected of having a surgical site infection or a patient suffering from a surgical site infection is measured. Such subjects are not particularly limited, so long as the surgical site infections are infections which are caused after surgery, and the subjects include patients suffering from an infection which is caused after surgery and requires an antimicrobial treatment, or a deteriorated infection (in particular, sepsis) which is caused after surgery.

Methods of measuring sCD14-ST are known, and the measurement can be carried out by various known analytical methods for proteins, for example, an immunoassay using an antibody or a biochemical assay such as electrophoresis, and an autoanalyzer for a clinical laboratory test can also be used. Analytical methods that use a substance with similar properties to those of an antibody, such as an RNA aptamer, are included in the present invention.

For example, Japanese Patent No. 4040666 discloses a method of measuring human sCD14-ST, more particularly, sandwich EIA systems using combinations of a polyclonal antibody (S68 antibody) or a monoclonal antibody (F1146-17-2 antibody), which were prepared using a peptide consisting of 16 amino acid residues of SEQ ID NO: 2 (the S68 peptide described in Japanese Patent No. 4040666) as an antigen, and anti-CD14-antigen monoclonal antibodies (for example, F1031-8-3 antibody, F1106-13-3 antibody, or the like) [Example 7-(1) in Japanese Patent No. 4040666], and these can be applied to the method of the present invention.

Further, as shown in the Examples described below, sCD14-ST can be measured using an automated chemiluminescent immunoassay analyzer (PATHFAST; manufactured by Mitsubishi Chemical Medience Corporation) by a chemiluminescent enzyme immunoassay using magnetic particles.

A sample used in the present invention is not particularly limited, so long as sCD14-ST can be measured. For example, blood samples (such as whole blood, plasma, or serum) may be used.

In the method of the present invention, an increase in the sCD14-ST concentration in a sample is used as an index of surgical site infections. For example, as shown in Example 2 described below, when an infection is caused after surgery, the sCD14-ST level increases. On day 7 after surgery, on which an infection was confirmed by culture, the sCD14-ST level was 978 pg/mL. This level was the same as that on day 5 after surgery. As described above, in the method of the present invention, when the sCD14-ST level shows a high value after surgery, it can be judged that an infection is caused, and it can be judged more easily and accurately in comparison with a conventional culture method. By contrast, when the sCD14-ST level shows a low value, it can be judged that no infections are caused. For example, when the sCD14-ST level in a sample is higher than a quantile value (for example, median) of healthy persons, it can be judged that an infection is caused. By contrast, when the sCD14-ST level in a sample is the same as or lower than a quantile value (for example, median) of healthy persons, it can be judged that no infections are caused. Further, the judgment may be carried out by statistical techniques such as Cox regression or logistic regression. As the criteria for judgment, a "threshold value" determined in advance can be used.

In the method of the present invention, although the threshold value for the sCD14-ST level in order to detect surgical site infections is expected to vary according to various conditions, such as sex or age, the threshold value for the judgment can be determined for those skilled in the art by appropriately selecting a suitable population that corresponds to the subjects, and statistically processing the data acquired from the population. As the population, a healthy person group, a non-infection group, an infection group, a sepsis group, septic groups of different pathological level, septic groups of different pathological types, or the like can be selected. In Example 2 described below, an optimal cutoff value of 891 pg/mL has been determined on the basis of the "average+2×SD" value of sCD14-ST concentration at the time when no infections were caused. In the method of the present invention, it is possible to automatically detect surgical site infections, without requiring judgment of a doctor, by determining the threshold value for the judgment, and comparing the measured sCD14-ST concentration in a sample with the threshold value for the judgment.

The cutoff value for detecting surgical site infections is preferably 200 to 5000 pg/mL, more preferably 300 to 3000 pg/mL, and most preferably 500 to 1000 pg/mL.

In the method of the present invention, although the time for sample collection is preferably at a stage where suspicion of surgical site infections has been raised, or a stage after the treatment, the sample may be collected over time after surgery. For example, the sample may be collected within about 7 to 10 days after surgery.

The kit of the present invention can be used for carrying out the method of the present invention and includes:

(a) an antibody specific to sCD14-ST;

(b) standard data showing a correlation between the amount of sCD14-ST in a sample and surgical site infections; and (c) an instruction manual.

The antibody used in the kit of the present invention may be a monoclonal antibody or a polyclonal antibody. Further, an antibody fragment that retains a specific binding activity to sCD14-ST, for example, Fab, Fab', $F(ab')_2$, or Fv, may be used in the kit.

Further, the antibody can be used, as it is, in the kit, or can be used in the kit in a suitable form based on the immunological technique to be employed, for example, by being immobilized onto a latex carrier when employing a latex agglutination immunoassay, by being immobilized onto magnetic particles when employing a highly sensitive measuring method using magnetic particles or the like, by being immobilized onto a substrate when employing a method that uses a substrate, such as an immunochromatography, or by being labeled with labeling substances (for example, enzymes, fluorescent substances, chemiluminescent substances, radioactive isotopes, biotin, or avidin) if necessary.

The standard data included in the kit of the present invention are not particularly limited, so long as they show a correlation between the amount of sCD14-ST in a sample and surgical site infections, and examples thereof include a threshold value for the judgment, and original data or statistically processed data for calculating the threshold value for the judgment. The standard data may be described in the instruction manual, or may be attached separately as a data sheet. Further, the form of the attached document includes paper, electronic media such as CD-ROM, and those downloaded from homepages or the like.

The instruction manual included in the kit of the present invention is not particularly limited, so long as it refers at least to the relationship between the amount of sCD14-ST in a sample and surgical site infections. In addition to the above reference, the instruction manual can include, for example, the explanation regarding the procedure for carrying out an immunological measurement using the kit of the present invention, the explanation regarding the procedure for predicting the prognosis based on the obtained measurement values, the precautions regarding the storage and handling of the kit per se, or the like.

EXAMPLES

The present invention now will be further illustrated by, but is by no means limited to, the following Examples.

Example 1

Methods of Measuring sCD14-ST and Procalcitonin

The measurement of sCD14-ST was carried out by modifying the method described in Example 7-(1) of Japanese Patent No. 4040666. More particularly, a polyclonal antibody (S68 antibody) labeled with alkaline phosphatase (ALP) and a monoclonal antibody (F1031-8-3 antibody) immobilized on magnetic particles (manufactured by JSR) were used, and the measurement was carried out using an automated chemiluminescent enzyme immunoassay analyzer (PATHFAST; manufactured by Mitsubishi Chemical Medience Corporation). The polyclonal antibody (S68 antibody) labeled with alkaline phosphatase (ALP) was prepared by preparing an Fab' fraction of the polyclonal antibody (S68 antibody) and linking the same with ALP by a maleimide method. CPD-star (manufactured by Applied Biosystems) was used as the luminescent substrate.

The measurement was carried out as follows. A sample was reacted with the antibody immobilized on magnetic particles and the ALP-labeled antibody, to form a complex composed of sCD14-ST contained in the sample and both antibodies. The complex was collected by a magnetic body to remove the unbound ALP-labeled antibody from the reaction mixture. The luminescent substrate was added to detect the amount of the luminescence as the amount of sCD14-ST.

The measurement of procalcitonin (PCT) was carried out using ECLusys (manufactured by Roche) and its dedicated measuring agent, ECLusys BRAHMS PCT (manufactured by Roche).

Example 2

Presence or Absence of Surgical Site Infections and Changes in Each Index Over Time With respect to a case (58 years old, male) in which no surgical site infections were caused after surgery of esophageal cancer, and a case (71 years old, male) in which a surgical site infection was caused, the relationship between the presence or absence, or timing of surgical site infections and each index was analyzed. More particularly, after 0, 1, 3, 5, and 7 days from surgery, EDTA whole blood samples or EDTA plasma samples were collected over time, and sCD14-ST and PCT were measured using the EDTA whole blood samples and the EDTA plasma samples, respectively. Additionally, a body temperature, a white blood cell count (WBC), and the number of SIRS-positive items were determined at each point in accordance with known methods. For example, with respect to the number of SIRS-positive items, a patient who satisfied two or more items out of the following items:

1) Body temperature >38° C. or <36° C.;
2) Heart rate >90 per minute;
3) Respiration rate >20 per minute or $PaCO_2$ >4.3 kPa; and
4) White blood cell count >12,000, <4,000/$m^3$ or immature leukocytes >10%;

was diagnosed with SIRS.

In the case in which a surgical site infection was caused, *Stenotrophomonas maltophilia* was detected in a sputum culture test on day 7 after surgery, and it was confirmed that an infection was caused.

Figure 2:
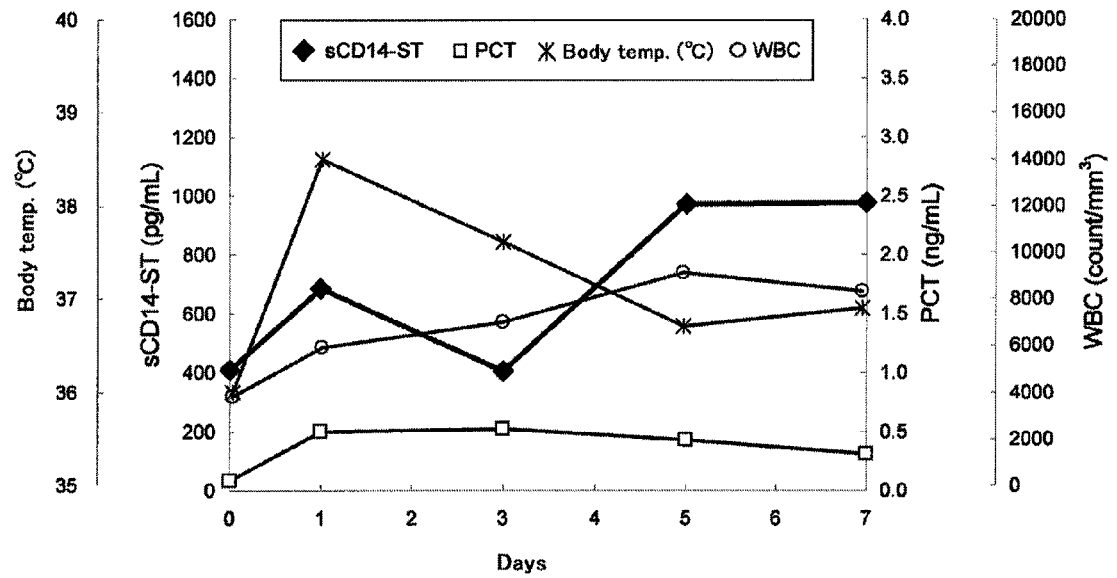
FIG. 2 is a graph showing the changes in each index (sCD14-ST, PCT, body temperature, and WBC) in a case in which a surgical site infection was caused.

The changes in each index in the case in which no surgical site infections were caused are shown in Table 1 and FIG. 1, and the changes in each index in the case in which a surgical site infection was caused are shown in Table 2 and FIG. 2.

In the case in which a surgical site infection was caused, an increase in the measured value of sCD14-ST was observed on day 5 after surgery, and this value was about 2.5 times as high as that on day 0 after surgery. This result was consistent with the above-mentioned event, and it was found that an infection could be detected at an early stage. By contrast, with respect to other indices, PCT, body temperature, WBC, and SIRS diagnosis, no significant changes were not shown in both cases, and the relationship with the infection was not observed, and thus, it was found that it was difficult to detect surgical site infections on the basis of these indices. Therefore, it was shown that sCD14-ST was effective as the method of the present invention for detecting surgical site infections.

Additionally, the "average+2×SD" value of sCD14-ST concentration at the time when no infections were caused was 891 pg/mL, and this result suggested that it could be judged that a patient suffered from a surgical site infection when the sCD14-ST concentration was about 900 pg/mL or more.

TABLE 1

| Items | sCD14-ST (pg/mL) | PCT (ng/mL) | Body temp. (° C.) | WBC (count/$mm^3$) | SIRS diagnosis (Number of positive items) |
|---|---|---|---|---|---|
| Immediately after surgery | 549 | 0.073 | 36.3 | 3600 | Non-SIRS (1) |
| Day 1 after surgery | 658 | 0.430 | 37.5 | 3880 | Non-SIRS (1) |

TABLE 1-continued

| Items | sCD14-ST (pg/mL) | PCT (ng/mL) | Body temp. (° C.) | WBC (count/mm$^3$) | SIRS diagnosis (Number of positive items) |
|---|---|---|---|---|---|
| Day 3 after surgery | 753 | 0.250 | 36.8 | 6830 | Non-SIRS (0) |
| Day 5 after surgery | 738 | 0.147 | 36.2 | 6210 | Non-SIRS (0) |
| Day 7 after surgery | 694 | 0.336 | 36.5 | 7380 | Non-SIRS (0) |

TABLE 2

| Items | sCD14-ST (pg/mL) | PCT (ng/mL) | Body temp. (° C.) | WBC (count/mm$^3$) | SIRS diagnosis (Number of positive items) |
|---|---|---|---|---|---|
| Immediately after surgery | 410 | 0.084 | 36.0 | 3810 | Non-SIRS (0) |
| Day 1 after surgery | 684 | 0.504 | 38.5 | 5920 | Non-SIRS (1) |
| Day 3 after surgery | 407 | 0.524 | 37.6 | 6980 | Non-SIRS (1) |
| Day 5 after surgery | 970 | 0.427 | 36.7 | 9090 | Non-SIRS (1) |
| Day 7 after surgery | 978 | 0.306 | 36.9 | 8340 | Non-SIRS (1) |

INDUSTRIAL APPLICABILITY

It was a surprising result that sCD14-ST, which was known as a marker for sepsis, could be used in specifically detecting not only severe systematic infections such as sepsis, but also infections not accompanied by SIRS. Additionally, since a marker for specifically detecting surgical site infections without being affected by surgery operations has not been known, it is so effective that sCD14-ST can be used in the present invention as a marker for judgment or detection of these events.

According to the present invention, a patient suspected of having a surgical site infection or a patient suffering from a surgical site infection can be detected easily and accurately, and it can be useful in determining a therapy at an early stage.

Although the present invention has been described with reference to specific embodiments, various changes and modifications obvious to those skilled in the art are possible without departing from the scope of the appended claims.

The invention claimed is:
1. A method of detecting and treating surgical site infections not accompanied by systemic inflammatory response syndrome, comprising the steps of:
   (A) collecting a sample from a patient after surgery suspected of having a surgical site infection not accompanied by systemic inflammatory response syndrome or a patient suffering from a surgical site infection not accompanied by systemic inflammatory response syndrome;
   (B) measuring sCD14-ST in the sample;
   (C) comparing the amount of sCD14-ST in the sample to a threshold value;

(D) diagnosing that the patient suffers from a surgical site infection not accompanied by systemic inflammatory response syndrome when an sCD14-ST value is higher than that of an uninfected person; and
(E) administering a treatment to the patient for the surgical site infection using an antimicrobial treatment.

2. The method according to claim 1, wherein the sCD14-ST value is compared to the threshold previously determined selected from the group consisting of a healthy person group, a non-infection group, an infection group, a sepsis group, septic groups of different pathological level, and septic groups of different pathological types.

3. The method according to claim 1, wherein sCD14-ST is measured by an immunoassay.

4. The method of claim 1, wherein sCD14-ST is measured in the sample within about 7 to 10 days after surgery.

5. A method of detecting and treating surgical site infections not accompanied by systemic inflammatory response syndrome, comprising the steps of:
(A) collecting a sample from a patient after surgery suspected of having a surgical site infection not accompanied by systemic inflammatory response syndrome or a patient suffering from a surgical site infection not accompanied by systemic inflammatory response syndrome;
(B) measuring sCD14-ST in the sample by an immunoassay using a kit for detecting surgical site infections not accompanied by systemic inflammatory response syndrome, comprising:
(i) an antibody specific to sCD14-ST, said antibody being immobilized onto a latex carrier, magnetic particles or a substrate, or being labeled with a labeling substance,
(ii) standard data showing a correlation between the amount of sCD14-ST in a sample and surgical site infections not accompanied by systemic inflammatory response syndrome,
(C) comparing the amount of sCD14-ST in the sample to a threshold value;
(D) diagnosing that the patient suffers from a surgical site infection not accompanied by systemic inflammatory response syndrome when an sCD14-ST value is higher than that of an uninfected person; and
(E) administering a treatment to the patient for the surgical site infection using an antimicrobial treatment.

6. The method of claim 5, wherein sCD14-ST is measured in the sample within about 7 to 10 days after surgery.

7. The method of claim 1, wherein sCD14-ST is measured in the sample within about 5 to 10 days after surgery.

8. The method of claim 5, wherein sCD14-ST is measured in the sample within about 5 to 10 days after surgery.

9. The method of claim 1, wherein sCD14-ST is measured using a kit for detecting surgical site infections not accompanied by systemic inflammatory response syndrome, the kit comprising:
(a) an antibody specific to sCD14-ST, said antibody being immobilized onto a latex carrier, magnetic particles or a substrate, or being labeled with a labeling substance,
(b) standard data showing a correlation between the amount of sCD14-ST in a sample and surgical site infections not accompanied by systemic inflammatory response syndrome, and
(c) an instruction manual.

* * * * *